(12) United States Patent
Rioux et al.

(10) Patent No.: US 11,592,509 B2
(45) Date of Patent: *Feb. 28, 2023

(54) SYSTEMS AND METHODS FOR RECONSTRUCTION OF DYNAMIC RESONANCE IMAGING DATA

(71) Applicant: NOVA SCOTIA HEALTH AUTHORITY, Halifax (CA)

(72) Inventors: James Rioux, Halifax (CA); Nathan Murtha, Ottawa (CA); Steven Beyea, Halifax (CA)

(73) Assignee: NOVA SCOTIA HEALTH AUTHORITY, Halifax (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/389,736

(22) Filed: Jul. 30, 2021

(65) Prior Publication Data

US 2021/0356546 A1 Nov. 18, 2021

Related U.S. Application Data

(63) Continuation of application No. 16/633,412, filed as application No. PCT/CA2018/050898 on Jul. 25, 2018, now Pat. No. 11,079,454.

(60) Provisional application No. 62/536,858, filed on Jul. 25, 2017.

(51) Int. Cl.
*G01R 33/563* (2006.01)
*A61B 5/055* (2006.01)
*G01R 33/54* (2006.01)
*G01R 33/56* (2006.01)

(52) U.S. Cl.
CPC ........ *G01R 33/56308* (2013.01); *A61B 5/055* (2013.01); *G01R 33/543* (2013.01); *G01R 33/5608* (2013.01)

(58) Field of Classification Search
None
See application file for complete search history.

(56) References Cited

U.S. PATENT DOCUMENTS 11,079,454 B2 * 8/2021 Rioux .............. G01R 33/56308

\* cited by examiner

*Primary Examiner* — Rodney E Fuller
(74) *Attorney, Agent, or Firm* — Hill & Schumacher

(57) ABSTRACT

Systems and methods are provided for performing automated reconstruction of a dynamic MRI dataset that is acquired without a fixed temporal resolution. On one or more image quality metrics (IQMs) are obtained by processing a subset of the acquired dataset. In one example implementation, at each stage of an iterative process, one or more IQMs of the image subset is computed, and the parameters controlling the reconstruction and/or the strategy for data combination are adjusted to provide an improved or optimal image reconstruction. Once the IQM of the image subset satisfies acceptance criteria based on an estimate of the overall temporal fidelity of the reconstruction, the full reconstruction can be performed, and the estimate of the overall temporal fidelity can be reported based on the IQM at the final iteration.

20 Claims, 3 Drawing Sheets

SYSTEMS AND METHODS FOR RECONSTRUCTION OF DYNAMIC RESONANCE IMAGING DATA

CROSS-REFERENCE TO RELATED APPLICATION

This application claims priority to U.S. Provisional Application No. 62/536,858, titled "SYSTEMS AND METHODS FOR RECONSTRUCTION OF DYNAMIC MAGNETIC RESONANCE IMAGING DATA" and filed on Jul. 25, 2017, the entire contents of which is incorporated herein by reference.

BACKGROUND

The present disclosure relates to reconstruction of images acquired with Magnetic resonance imaging (MRI).

Magnetic resonance imaging is commonplace in clinical settings for diagnosis and monitoring of a wide variety of diseases. Unlike X-ray or computed tomography (CT) scans, MRI does not require ionizing radiation and can produce images with a variety of contrasts to highlight injuries or distinguish healthy from abnormal tissue. In addition to providing single static images that depict anatomical structures, MRI can also be used to acquire multiple images in a time series. Common applications for such dynamic imaging include cardiac imaging (to image the heart as it beats) or contrast-enhanced imaging (to watch the inflow of an injected contrast agent that can highlight abnormalities in blood vessels or help depict tumors).

One limitation of MRI as compared to other kinds of medical imaging technologies is that it takes some time to produce images. Depending on factors such as the imaging method, the field of view and the desired spatial resolution, high-quality diagnostic images may take between several seconds and several minutes to acquire. To accurately measure dynamic physiological processes, higher speed is often necessary, but speeding up MRI scans has traditionally come at the cost of spatial resolution (meaning that smaller features cannot be easily seen) or reduced quality (images become noisy or grainy and it is harder to see subtle changes in contrast).

Several recent advances in image processing have allowed for accurate reconstruction of highly undersampled data—that is, only a fraction of the full dataset is acquired, with the remainder synthesized in post-processing to yield a complete image. This directly reduces imaging time and can be used to improve the temporal resolution of dynamic MRI scans without sacrificing as much quality as would otherwise occur. Some acceleration methods such as parallel imaging rely on specialized RF coil hardware, while others such as compressed sensing (CS) rely only on certain assumptions about the structure of the underlying data.

Multiple choices affect the quality of images reconstructed with CS. The most important is the undersampling factor (e.g. in a case where 25% of the total data is collected, the acquisition time is sped up by a factor of 4), but the undersampling pattern (which specific subset of the dataset is sampled), the parameters that control how new data are synthesized, and the algorithm by which this synthesis is performed can all impact the resulting image quality. Most studies of CS in MRI focus on the degree of undersampling, choosing a value that achieves a certain goal in terms of scan time.

According to conventional practice, empirical testing is then performed to determine which sampling strategy, algorithm and parameters yield acceptable image quality at the selected undersampling factor (acceleration factor). This is often judged by a small number of researchers based on a limited pool of test data, and may not generalize well to larger studies in different areas of anatomy, studies using different scan methods, and other variations.

According to typical CS implementations, image quality is generally only assessed after performing CS reconstruction. The image quality is usually assessed with one of several standardized metrics, most of which are used to compare accelerated images (images obtained through undersampling) with their unaccelerated counterparts, in order to assess the residual degradation after reconstruction.

Dynamic MRI poses additional challenges for CS reconstruction but also provides opportunities for improved acquisition strategies. When CS is used to accelerate each individual image in a time series, the choice of undersampling factor determines the temporal resolution of the scan. However, the optimal temporal resolution is not always known beforehand. For example, choosing slow temporal resolution to maintain image quality may lead to rapid dynamics being overlooked, and high temporal resolution may degrade image quality and make diagnosis difficult.

One alternative is to acquire data in such a way that there is no defined temporal resolution, and data can instead be processed to yield multiple temporal resolutions. This can be achieved, for example, using golden angle sampling, which ensures that any arbitrary subset of data has near-uniform coverage, while ensuring that subsequent k-space radial spokes do not overlap with previously acquired spokes. For example, as shown in FIG. 1, the subset including N=5 radial spokes and the subset containing N=11 radial spokes both have relatively uniform azimuthal coverage of k-space.

Using such a method, it is possible to reconstruct data at high spatial resolution and low temporal resolution, or vice-versa, or any intermediate combination. However, the method does not provide a prescription for determining a suitable temporal resolution that balances the quality of the individual images with that of the time information contained in the series. An optimal temporal resolution that balances spatial image quality with temporal information will typically vary based on the desired application. For example, an optimal temporal resolution may depend on whether the images are being presented directly to a radiologist for review, or whether data will be further processed to extract features for automatic classification based on machine learning.

Furthermore, in addition to selecting a temporal resolution for reconstruction, a suitable reconstruction algorithm and associated parameters should also be selected. These choices will also likely vary with the desired application, and may even vary on an individual basis, such that choices which perform well for a dataset from one patient may not be optimal for a similar dataset from a different patient.

SUMMARY

The present disclosure provides systems and methods for automated reconstruction of a dynamic MRI dataset acquired without a fixed temporal resolution. This reconstruction method is based on one or more image quality metrics (IQMs) that are obtained by processing a subset of the acquired dataset. In one example implementation, at each stage of an iterative process, one or more IQMs of the image subset is computed, and the parameters controlling the reconstruction and/or the strategy for data combination are adjusted to provide an improved or optimal image reconstruction. Once the IQM of the image subset satisfies acceptance criteria based on an estimate of the overall temporal fidelity of the reconstruction, the full reconstruction can be performed, and the estimate of the overall temporal fidelity can be reported based on the IQM at the final iteration.

Accordingly, in one aspect, there is provided a method of performing dynamic magnetic resonance imaging, the method comprising:

a) controlling a magnetic resonance imaging scanner to generate a sequence of RF pulses and detect RF signals that are responsively emitted by a subject positioned with a bore of the magnetic resonance imaging scanner, thereby obtaining an input dataset, wherein the sequence of RF pulses is selected to facilitate image reconstruction according to a plurality of temporal resolutions;

b) partitioning the input dataset to generate an image series of non-reconstructed image data, the image series having a selected temporal resolution;

c) selecting an image subset from the image series;

d) performing image reconstruction on the image subset, thereby obtaining a reconstructed image subset;

e) processing the image subset to determine one or more image quality metrics;

f) comparing the image quality metrics to pre-selected criteria associated with an estimated fidelity of a full reconstruction of the input dataset;

g) in the event that the one or more image quality metrics do not satisfy the pre-selected criteria, adjusting the temporal resolution and repeating operations b) to f); and h) in the event that the one or more image quality metrics satisfy the pre-selected criteria, employing the current temporal resolution to perform full reconstruction on the input dataset.

In another aspect, there is provided a magnetic resonance imaging system comprising:

a magnetic resonance imaging scanner; and control and processing hardware operatively coupled to said magnetic resonance imaging scanner, wherein said control and processing hardware comprises memory coupled with one or more processors to store instructions, which when executed by the one or more processors, causes the one or more processors to perform operations comprising:

a) controlling said magnetic resonance imaging scanner to generate a sequence of RF pulses and detect RF signals that are responsively emitted by a subject positioned with a bore of said magnetic resonance imaging scanner, thereby obtaining an input dataset, wherein the sequence of RF pulses is selected to facilitate image reconstruction according to a plurality of temporal resolutions;

b) partitioning the input dataset to generate an image series of non-reconstructed image data, the image series having a selected temporal resolution;

c) selecting an image subset from the image series;

d) performing image reconstruction on the image subset, thereby obtaining a reconstructed image subset;

e) processing the image subset to determine one or more image quality metrics;

f) comparing the image quality metrics to pre-selected criteria associated with an estimated fidelity of a full reconstruction of the input dataset;

g) in the event that the one or more image quality metrics do not satisfy the pre-selected criteria, adjusting the temporal resolution and repeating operations b) to f); and h) in the event that the one or more image quality metrics satisfy the pre-selected criteria, employing the current temporal resolution to perform full reconstruction on the input dataset.

In another aspect, there is provided a method of performing dynamic magnetic resonance imaging, the method comprising:

a) controlling a magnetic resonance imaging scanner to generate a sequence of RF pulses and detect RF signals that are responsively emitted by a subject positioned with a bore of the magnetic resonance imaging scanner, thereby obtaining an input dataset, wherein the sequence of RF pulses is selected to facilitate image reconstruction according to a plurality of temporal resolutions;

b) partitioning the input dataset to generate an image series of non-reconstructed image data, the image series having a selected temporal resolution;

c) performing image reconstruction on the image series, thereby obtaining a set of reconstructed image frames;

d) selecting an image subset of reconstructed image frames from the set of reconstructed image frames;

e) processing the image subset to determine one or more image quality metrics;

f) comparing the image quality metrics to pre-selected criteria associated with an estimated fidelity of a full reconstruction of the input dataset;

g) in the event that the one or more image quality metrics do not satisfy the pre-selected criteria, adjusting the temporal resolution and repeating operations b) to f); and h) in the event that the one or more image quality metrics satisfy the pre-selected criteria, employing the current temporal resolution to perform full reconstruction on the input dataset.

In another aspect, there is provided a magnetic resonance imaging system comprising:

a magnetic resonance imaging scanner; and control and processing hardware operatively coupled to said magnetic resonance imaging scanner, wherein said control and processing hardware comprises memory coupled with one or more processors to store instructions, which when executed by the one or more processors, causes the one or more processors to perform operations comprising:

a) controlling said magnetic resonance imaging scanner to generate a sequence of RF pulses and detect RF signals that are responsively emitted by a subject positioned with a bore of said magnetic resonance imaging scanner, thereby obtaining an input dataset, wherein the sequence of RF pulses is selected to facilitate image reconstruction according to a plurality of temporal resolutions;

b) partitioning the input dataset to generate an image series of non-reconstructed image data, the image series having a selected temporal resolution;

c) performing image reconstruction on the image series, thereby obtaining a set of reconstructed image frames;

d) selecting an image subset of reconstructed image frames from the set of reconstructed image frames;

e) processing the image subset to determine one or more image quality metrics;

f) comparing the image quality metrics to pre-selected criteria associated with an estimated fidelity of a full reconstruction of the input dataset;

g) in the event that the one or more image quality metrics do not satisfy the pre-selected criteria, adjusting the temporal resolution and repeating operations b) to f); and h) in the event that the one or more image quality metrics satisfy the pre-selected criteria, employing the current temporal resolution to perform full reconstruction on the input dataset.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
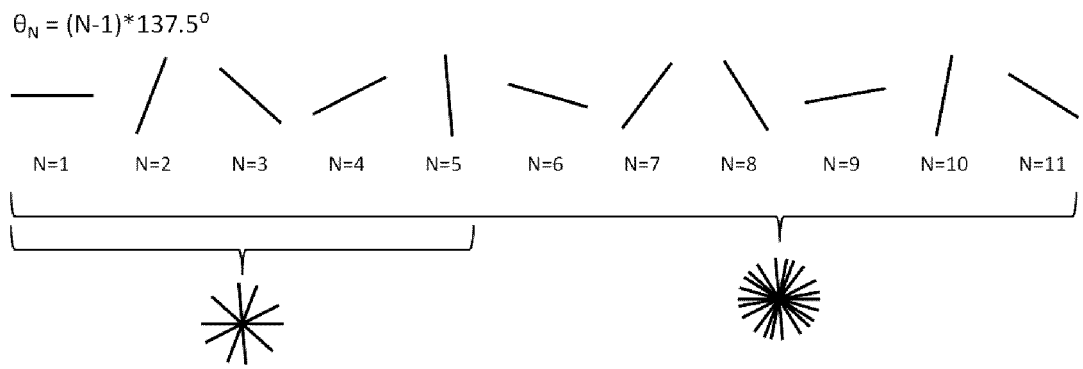
FIG. 1 illustrates examples of selecting different temporal resolutions of undersampled MRI data based on golden angle sampling, demonstrating how the different temporal resolutions retain uniform sampling density.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the term "undersampled data" refers to any acquisition of MRI data in which the data collected are insufficient to produce an image free of aliasing artifacts (according to the Nyquist criterion for the desired image's field of view and resolution) in at least one dimension.

The present disclosure provides systems and methods for performing reconstruction of undersampled dynamic or time-resolved MRI data, based on automated assessment of image quality as measured by one or more metrics, in order to provide a dataset of maximal fidelity according to specified criteria. As explained in detail below, example reconstruction methods of the present disclosure are based on one or more image quality metrics (IQMs) that are obtained by processing a subset of the acquired dataset. Image reconstruction may be performed according to an iterative method, where at each iteration, one or more IQMs of the image subset is computed, and the parameters controlling the reconstruction and/or the strategy for data combination are adjusted provide an improved or optimal image reconstruction. Once the IQM of the image subset satisfies acceptance criteria based on an estimate of the overall temporal fidelity of the reconstruction, the full reconstruction can be performed, and the estimate of the overall temporal fidelity can be reported based on the IQM at the final iteration. The methods of the present disclosure are motivated by a recent discovery by the inventors that predictable relationships exist between the quality of individual images within a dynamic MRI time series, as measured by appropriate metrics, and parameters that relate to the quality of the overall time series, such as the accuracy of model fits to the data.

Figure 3:
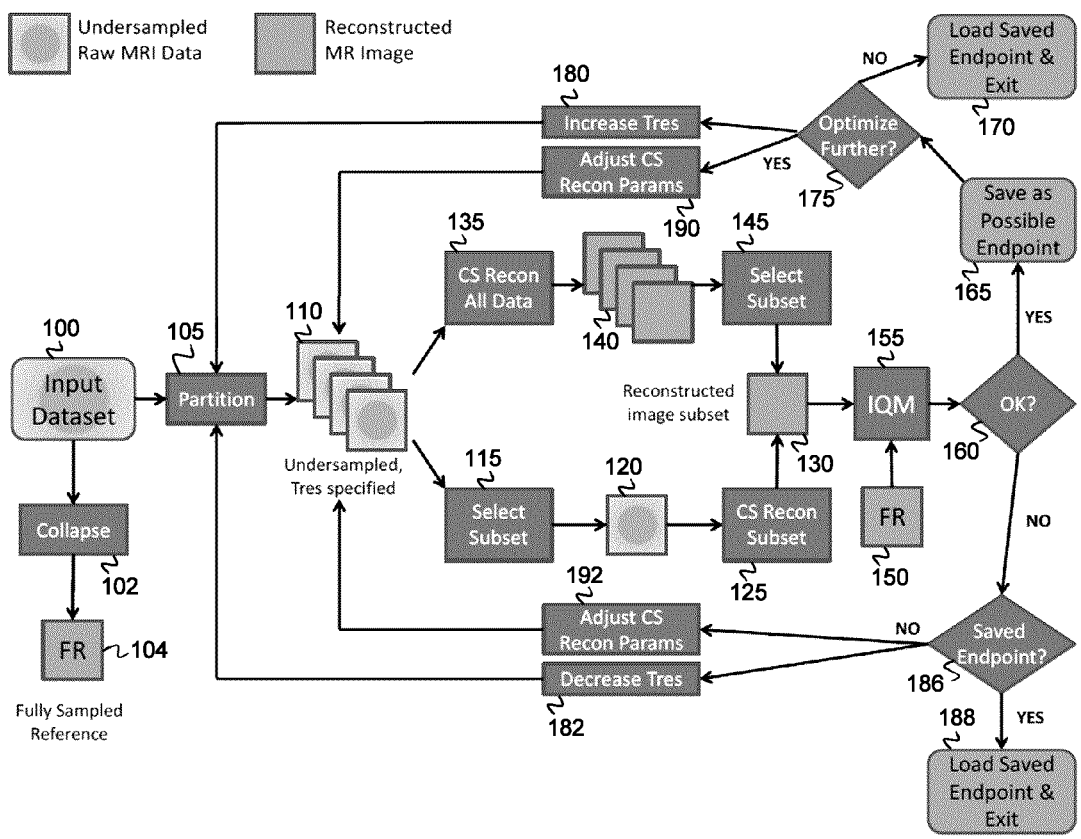
FIG. 3 is a flowchart illustrating an example method of iterative and automated dynamic MRI reconstruction based on measurement of image quality metric(s) (IQM) performed on a subset of data.

Referring now to FIG. 3, a flowchart is provided that illustrates an example method of performing image reconstruction of dynamic MRI data. According to a first step, a patient or subject is scanned according to pulse sequence that facilitates the acquisition of MRI data without enforcing a pre-determined temporal resolution. For example, a pulse sequence may be employed whereby the MRI data is acquired as a series of fundamental units (e.g. k-space segments). Examples of such pulse sequence generation and MRI data acquisition methods include, but are not limited to, radial spokes incremented by the golden angle (as illustrated in FIG. 1), spiral interleaves, or, for example, a group of samples prescribed according to a strategy that minimizes overlap between nearby groups (e.g. Poisson-disc or CIRcular Cartesian UnderSampling (CIRCUS)). The acquisition of the MRI data provides an input dataset (an acquired dataset), as shown at 100.

As shown at step 110, the input dataset is partitioned to produce an image series (a series of image data that has not yet been reconstructed) with an initial temporal resolution ($T_{res}$), where the partitioned image series is shown at 110. Based on the desired application, an initial temporal resolution $T_{res}$ can be selected to partition the data into groups of N units, the groups forming a series of undersampled images to be reconstructed. The initial temporal resolution may be determined or prescribed based on the application; for example, in dynamic contrast-enhanced imaging of the prostate, the PI-RADS criteria developed by the American College of Radiology suggest a temporal resolution of 7 seconds.

As explained above, the input dataset may be acquired as a series of fundamental units that support image processing according to a wide range of selectable temporal resolutions. Each fundamental unit of data will take some time T to acquire, and will sample R % of the total available data. Combining the data in groups of N units will generally produce an image series with temporal resolution $T_{res}=T*N$. Higher temporal resolution (small values of T*N) allows better depiction of rapidly-changing behavior throughout the image series. At the same time, assuming minimal overlap between groups, the total percentage of data sampled by each image in the series is R*N %, and higher sampling (large values of R*N) will generally lead to higher-fidelity images, though with more advanced sampling strategies some mitigation of this trade-off is possible.

In many implementations of the present example embodiment, the undersampling factor R*N will be significantly less than 100%, and reconstruction with a technique based on Compressed Sensing (CS) principles will be employed to remove artifacts from undersampling and otherwise improve image quality.

Some CS algorithms operate on individual images without knowledge of any temporal evolution (e.g. this is an option in the BART toolkit). In such cases, the IQM analysis may be performed based the extraction and processing of only a subset of the acquired image data. A subset of the partitioned image series is selected for subsequent reconstruction and image quality analysis in step 115. The subset of the partitioned image series is in the form of undersampled raw MRI data, as shown at 120. The subset of the partitioned image series is then reconstructed, as shown at 125, according to a desired reconstruction algorithm, thereby yielding a reconstructed image subset suitable for IQM analysis. In some example implementations, a common subset is employed during each iteration. In other example implementations, the subset may vary among iterations.

In some example implementations, a single representative frame of image data, such as the first frame of image data in the image series, may be selected as the image subset. In another example embodiment, two or more frames of image data may be selected from the partitioned image series. For example, a subset could include one frame of image data from the beginning of the time series and another from near the end. Such an implementation would result in the generation of one or more IQMs for each frame, which could then either be averaged or kept separate.

However, other CS algorithms employ an assumption of the temporal dynamics (e.g. REPCOM) or estimate the temporal dynamics from the underlying data without requiring a priori assumptions (e.g. Blind CS or BCS). In such cases, prior to extracting a subset for image quality metric (IQM) analysis, the full acquired dataset (i.e. the complete time series) is reconstructed, as shown at 135. This generates a set of reconstructed images (140) from which a suitable subset can be selected (145) and sent for IQM analysis.

Once an image subset is reconstructed (shown at 130), it is evaluated using one or more image quality metrics (IQMs).

IQMs can be classified as full-reference (in which a degraded image is compared to a known reference image) or no-reference (in which an image is evaluated without such a reference). In the case of CS reconstruction, an ideal reference image is often computed from fully sampled data, but for accelerated individual MRI scans, such fully-sampled reference images are generally not available. However, with dynamic MRI it is often possible to select a sampling strategy such that each possible sample is collected at least once during the scan, if not during each temporal frame. The temporal frames can then be collapsed into a single image, as shown at 102, which, though it not longer contains any information about temporal evolution, does have sufficient sampling density to ensure a high-quality reconstruction 104 that is suitable as a reference. Such a fully sampled reference is labeled FR in FIG. 3 and shown again at 150 as an input to the generation of the one or more IQMs at 155.

In an alternative example implementation, no-reference IQMs for MRI are now being developed which may allow the evaluation of CS reconstructions without the need for comparison with a reference image.

In either case, the result of IQM analysis 155 (examples of which are described further below) can be used to estimate temporal fidelity of the fully reconstructed dataset at 160 according to various example criteria. Examples of suitable IQMs include root-mean-square error (RMSE), Structural Similarity index (SSIM) and its variants (such as the Multiscale SSIM and Information-Weighted SSIM), and Feature Similarity Index (FSIM).

Figure 2:
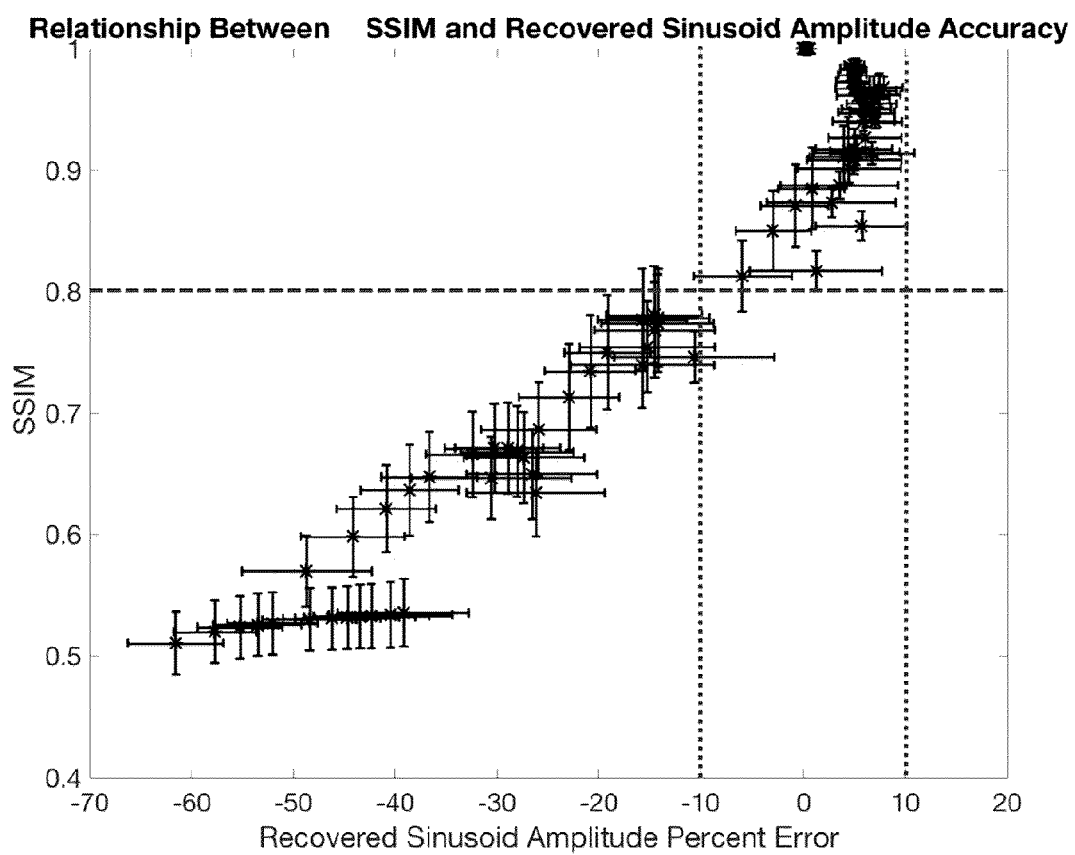
FIG. 2 graphically demonstrates an example relationship between an image quality metric of a subset of the acquired MRI data (as measured by Multi-Scale Structural Similarity index, MSSIM) and image series quality (as measured by percent error in a fitted model parameter) for simulated MRI data.

In some example embodiments, the temporal fidelity of the fully reconstructed dataset may be estimated using a relationship between a selected IQM and performance data obtained when undersampling a reference image. FIG. 2 shows an example implementation in which a simulated MRI dataset was constructed with portions of the image made to evolve sinusoidally, i.e. their intensity rises and falls over time with a given amplitude A, frequency B and phase C according to:

$$S(t)=A \sin(Bt+C)$$

The dataset was then undersampled to varying degrees (ranging from R=1.5 to R=12, using a CIRCUS strategy for golden-angle Cartesian sampling) and reconstructed using BART. An IQM (SSIM in this example) was computed for the first image in the series as compared to the known fully-sampled reference image. The intensity of the sinusoidally evolving portions were fitted with the mathematical model described above, such that the observed frequency and amplitude of the evolution can be compared to the known original frequency and amplitude, with degradation expressed in terms of percent error. In this case, if it is desired to maintain accuracy to within +/−10%, it is necessary to ensure that the SSIM is above 0.8. Similar relationships for other IQMs and measures of temporal fidelity may alternatively be employed.

Referring again to FIG. 3, as shown at 165, if a given IQM is evaluated at 160 and found to satisfy pre-selected a performance criterion or criteria (i.e. if the IQM is found to be in an acceptable range for a desired application), then the algorithm can terminate as shown at 170.

Alternatively, in the event that a given IQM is evaluated and found to satisfy pre-selected a performance criterion or criteria, the latest parameter set can be saved as a potential endpoint and further optimization can be attempted, as shown at the "yes" output of decision 175. For example, if the image quality is deemed to be acceptable at a given temporal resolution, it may still be beneficial to improve the temporal resolution (as shown at 180) without a significant sacrifice on spatial resolution and therefore the range of dynamics that can be observed, so long as the IQM is not significantly decreased by doing so.

In the event that a given IQM is evaluated at 160 and is found to fail the pre-selected acceptance criterion or criteria, then the algorithm can proceed with one or more further iterations with a decreased $T_{res}$, as shown at 182. Alternatively, the process can be terminated in the event that a pre-selected maximum number of iterations have occurred, saving the most recent parameter set, as shown at 186 and 188.

In some example embodiments, parameters that govern the reconstruction (such as the regularization weight or weights, or other parameters specific to the particular algorithm being used) can be adjusted addition to $T_{res}$, in order to attempt to improve the IQM and therefore the quality of the overall time series. In one example implementation, such parameter adjustments can be made, for example, through one or more additional iterations that are performed for each $T_{res}$. If the acceptance criterion or criteria are not met after such iterations, then $T_{res}$ may be increased (the temporal resolution becoming coarser), sacrificing the ability to perceive fast dynamics to produce a gain in image quality, which may depend on the desired application of the data.

In another example implementation, such parameter adjustments can be made, for example, through one or more additional iterations that are performed after having satisfied the acceptance criteria or criterion at 160, in order to further optimize the reconstruction. If it is found that such adjustments do not have a net benefit, the algorithm can revert to the best available saved endpoint and exit.

Figure 4:
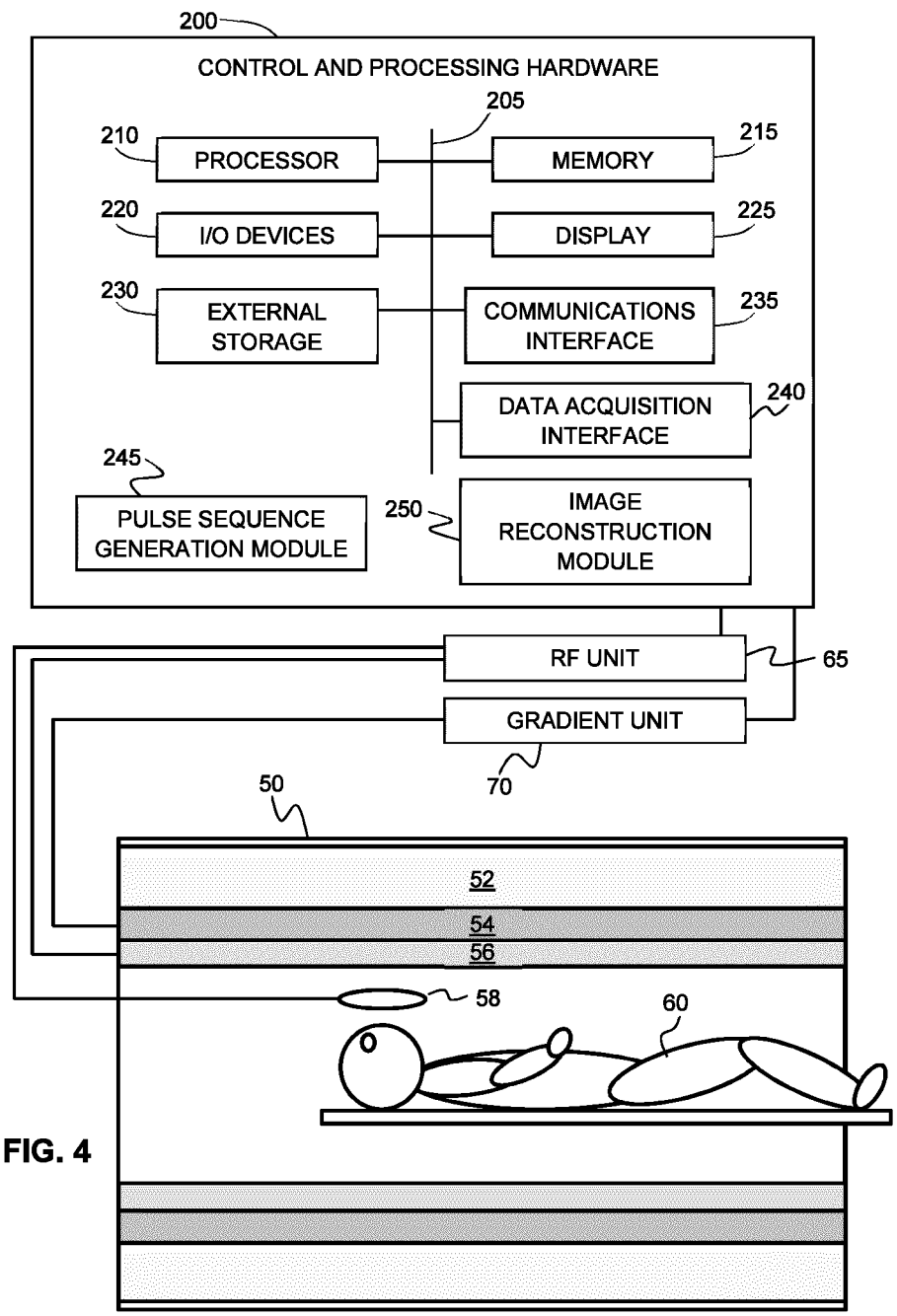
FIG. 4 is a block diagram of an example system for performing automated dynamic MRI reconstruction.

Referring now to FIG. 4, an example system is illustrated for performing dynamic reconstruction with an MRI system according to the example methods described above. The example system includes a magnetic resonance scanner 50 that employs a main magnet 52 to produce a main magnetic field BO, which generates a polarization in a patient 60 or the examined subject. The example system includes gradient coils 54 for generating magnetic field gradients. A receive coil 58 detects RF signals from patient 60. The receive coil 58 can also be used as a transmission coil for the generation of radio frequency (RF) pulses. Alternatively, a body coil 56 may be employed to radiate and/or detect RF pulses. The RF pulses are generated by an RF unit 65, and the magnetic field gradients are generated by a gradient unit 70.

It will be understood that the MR system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

In the example system shown in FIG. 4, a control and processing hardware 200 controls the MRI scanner to generate RF pulses according to a suitable pulse sequence. The control and processing hardware 200 is interfaced with the MRI scanner 50 for controlling the acquisition of the received MRI signals. The control and processing hardware 200 acquires the received MRI signals from the RF unit 65 and processes the MRI signals according to the methods described herein in order to perform image reconstruction and generate MRI images.

The control and processing hardware 200 may be programmed with a set of instructions which when executed in the processor causes the system to perform one or more methods described in the present disclosure. For example, as shown in FIG. 4, control and processing hardware 200 may be programmed with instructions in the form of a set of executable image processing modules, such as, but not limited to, a pulse sequence generation module 245 and an image reconstruction module 250. The pulse sequence generation module 245 may be implemented using algorithms known to those skilled in the art for pulse sequence generation, such as those described above.

During MRI scanning, RF data is received from the RF coils 56 and/or 58. The pulse sequence generation module 245 establishes the sequence of RF pulses and magnetic field gradients depending on the desired imaging sequence, MR signals responsively emitted by the patient and detected by the coils 56 and/or 58 are acquired. The image reconstruction module 245 processes the acquired MRI signals to perform image reconstruction and MRI image generation according to the example method shown in FIG. 3, or variations thereof.

The control and processing hardware 200 may include, for example, one or more processors 210, memory 215, a system bus 205, one or more input/output devices 220, and a plurality of optional additional devices such as communications interface 235, data acquisition interface 240, display 225, and external storage 230.

It is to be understood that the example system shown in FIG. 4 is illustrative of a non-limiting example embodiment, and is not intended to be limited to the components shown. For example, the system may include one or more additional processors and memory devices. Furthermore, one or more components of control and processing hardware 200 may be provided as an external component that is interfaced to a processing device.

Some aspects of the present disclosure can be embodied, at least in part, in software, which, when executed on a computing system, configures the computing system as a specialty-purpose computing system that is capable of performing the signal processing and noise reduction methods disclosed herein, or variations thereof. That is, the techniques can be carried out in a computer system or other data processing system in response to its processor, such as a microprocessor, CPU or GPU, executing sequences of instructions contained in a memory, such as ROM, volatile RAM, non-volatile memory, cache, magnetic and optical disks, cloud processors, or other remote storage devices. Further, the instructions can be downloaded into a computing device over a data network, such as in a form of a compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), network attached storage, cloud storage, among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing image reconstruction of dynamic magnetic resonance image data, the method comprising:
   a) partitioning the dynamic magnetic resonance image data to generate an image series of non-reconstructed image data, the image series having a selected temporal resolution;
   b) selecting an image subset from the image series;
   c) performing image reconstruction on the image subset, thereby obtaining a reconstructed image subset;
   d) processing the reconstructed image subset to determine one or more image quality metrics;
   e) determining that the one or more image quality metrics fail to satisfy pre-selected criteria; and
   f) repeating steps (a) to (d) one or more times, each time generating and employing an image series having a different selected temporal resolution, until the one or more image quality metrics satisfy the pre-selected criteria, thereby determining a suitable temporal resolution for satisfying the one or more image quality metrics; and
   g) employing the suitable temporal resolution perform full reconstruction on the dynamic magnetic resonance image data.

2. The method according to claim 1 further comprising communicating a measure associated with an estimated temporal fidelity of a full reconstruction of the dynamic magnetic resonance image data.

3. The method according to claim 1 wherein the dynamic magnetic resonance image data is an undersampled image dataset, and such that reconstruction is performed according to a compressed sensing method.

4. The method according to claim 1 wherein at least one image quality metric is based on a Structural Similarity index.

5. The method according to claim 1 wherein one or more of the image quality metrics is generated based on a comparison with a reference image.

6. The method according to claim 5 wherein the reference image is generated by collapsing temporal frames of the dynamic magnetic resonance image data into a single image.

7. The method according to claim 1 further comprising, after performing step (f) and prior to performing step (g):
   performing the following steps one or more times to improve one or more of temporal fidelity and image quality:
   h) varying one or more reconstruction parameters;
   i) performing image reconstruction on the image subset generated using the selected temporal resolution, thereby obtaining the reconstructed image subset; and
   j) processing the reconstructed image subset to determine the one or more image quality metrics;
   wherein step (g) is performed using reconstruction parameters associated with improved image quality metrics.

8. The method according to claim 1 further comprising, after performing step (e) and prior to performing step (f):
   performing the following steps one or more times to improve one or more of temporal fidelity and image quality:
   h) varying one or more reconstruction parameters;
   i) performing image reconstruction on the image subset, thereby obtaining the reconstructed image subset; and
   j) processing the reconstructed image subset to determine the one or more image quality metrics;
   wherein steps (f) and (g) are performed using reconstruction parameters associated with improved image quality metrics.

9. An image processing system for performing image reconstruction on dynamic magnetic resonance image data, the image processing system comprising:
   control and processing hardware comprising memory coupled with one or more processors to store instructions, which when executed by the one or more processors, causes the one or more processors to perform operations comprising:
   a) partitioning the dynamic magnetic resonance image data to generate an image series of non-reconstructed image data, the image series having a selected temporal resolution;
   b) performing image reconstruction on a selected image subset from the image series, thereby obtaining a reconstructed image subset;
   c) processing the reconstructed image subset to determine one or more image quality metrics;
   d) determining that the one or more image quality metrics fail to satisfy pre-selected criteria; and
   e) repeating steps (a) to (c) one or more times, each time generating and employing an image series having a different selected temporal resolution, until the one or more image quality metrics satisfy the pre-selected criteria, thereby determining a suitable temporal resolution for satisfying the one or more image quality metrics; and
   f) employing the suitable temporal resolution perform full reconstruction on the dynamic magnetic resonance image data.

10. The system according to claim 9 wherein said control and processing hardware is configured to communicate a measure associated with an estimated temporal fidelity of the full reconstruction of the dynamic magnetic resonance image data.

11. The system according to claim 9 wherein said control and processing hardware is configured such that the dynamic magnetic resonance image data is an undersampled image dataset, and such that reconstruction is performed according to a compressed sensing method.

12. The system according to claim 9 wherein said control and processing hardware is configured such that at least one image quality metric is based on a Structural Similarity index.

13. The system according to claim 9 wherein said control and processing hardware is configured such that one or more of said image quality metrics is generated based on a comparison with a reference image.

14. The system according to claim 13 wherein said control and processing hardware is configured such that said reference image is generated by collapsing temporal frames of the dynamic magnetic resonance image data into a single image.

15. The system according to claim 9 wherein said control and processing hardware is configured to perform the following operations one or more times to improve one or more of temporal fidelity and image quality, after performing step (e) and prior to performing step (f):
   g) varying one or more reconstruction parameters;
   h) performing image reconstruction on the selected image subset generated using the selected temporal resolution, thereby obtaining the reconstructed image subset; and
   i) processing the reconstructed image subset to determine the one or more image quality metrics;
   wherein step (f) is performed using reconstruction parameters associated with improved image quality metrics.

16. The system according to claim 9 wherein said control and processing hardware is configured to perform the following operations one or more times to improve one or more of temporal fidelity and image quality, after performing step (d) and prior to performing step (e):
   performing the following steps one or more times to improve one or more of temporal fidelity and image quality:
   g) varying one or more reconstruction parameters;
   h) performing image reconstruction on the selected image subset, thereby obtaining the reconstructed image subset; and
   i) processing the reconstructed image subset to determine the one or more image quality metrics;
   wherein steps (e) and (f) are performed using reconstruction parameters associated with improved image quality metrics.

17. A non-transitory computer-readable storage medium having stored therein data representing instructions executable by a processor for performing image reconstruction of dynamic magnetic resonance image data, the storage medium comprising instructions for performing operations including:
   a) partitioning the dynamic magnetic resonance image data to generate an image series of non-reconstructed image data, the image series having a selected temporal resolution;
   b) performing image reconstruction on a selected image subset from the image series, thereby obtaining a reconstructed image subset;
   c) processing the reconstructed image subset to determine one or more image quality metrics;
   d) determining that the one or more image quality metrics fail to satisfy pre-selected criteria; and
   e) repeating steps (a) to (c) one or more times, each time generating and employing an image series having a different selected temporal resolution, until the one or more image quality metrics satisfy the pre-selected criteria, thereby determining a suitable temporal resolution for satisfying the one or more image quality metrics; and
   f) employing the suitable temporal resolution perform full reconstruction on the dynamic magnetic resonance image data.

18. A method of image reconstruction of dynamic magnetic resonance image data, the method comprising:
   a) partitioning the dynamic magnetic resonance image data to generate an image series of non-reconstructed image data, the image series having a selected temporal resolution;
   b) performing image reconstruction on the image series, thereby obtaining a set of reconstructed image frames;
   c) selecting a subset of reconstructed image frames from the set of reconstructed image frames;
   d) processing the subset of reconstructed image frames to determine one or more image quality metrics;
   e) determining that the one or more image quality metrics fail to satisfy pre-selected criteria; and
   f) repeating steps (a) to (d) one or more times, each time generating and employing an image series having a different selected temporal resolution, until the one or more image quality metrics satisfy the pre-selected criteria.

19. An imaging processing system for performing image reconstruction on dynamic magnetic resonance image data, the imaging processing system comprising:
   control and processing hardware comprising memory coupled with one or more processors to store instructions, which when executed by the one or more processors, causes the one or more processors to perform operations comprising:
   a) partitioning the dynamic magnetic resonance image data to generate an image series of non-reconstructed image data, the image series having a selected temporal resolution;
   b) performing image reconstruction on the image series, thereby obtaining a set of reconstructed image frames;
   c) processing a selected subset of the reconstructed image frames to determine one or more image quality metrics;
   d) determining that the one or more image quality metrics fail to satisfy pre-selected criteria; and
   e) repeating steps (a) to (c) one or more times, each time generating and employing an image series having a different selected temporal resolution, until the one or more image quality metrics satisfy the pre-selected criteria.

20. A non-transitory computer-readable storage medium having stored therein data representing instructions executable by a processor for performing image reconstruction of dynamic magnetic resonance image data, the storage medium comprising instructions for performing operations including:
   a) partitioning the dynamic magnetic resonance image data to generate an image series of non-reconstructed image data, the image series having a selected temporal resolution;
   b) performing image reconstruction on the image series, thereby obtaining a set of reconstructed image frames;
   c) processing a selected subset of the reconstructed image frames to determine one or more image quality metrics;
   d) determining that the one or more image quality metrics fail to satisfy pre-selected criteria; and
   e) repeating steps (a) to (c) one or more times, each time generating and employing an image series having a different selected temporal resolution, until the one or more image quality metrics satisfy the pre-selected criteria.

* * * * *